(12) United States Patent
Bradfield et al.

(10) Patent No.: US 6,432,692 B1
(45) Date of Patent: Aug. 13, 2002

(54) SENSITIVE BIOASSAY FOR DETECTING AGONISTS OF THE ARYL HYDROCARBON RECEPTOR

(75) Inventors: Christopher A. Bradfield, Madison, WI (US); Lucy A. Carver, San Diego, CA (US); Elizabeth E. Dunham, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/337,307

(22) Filed: Jun. 21, 1999

(51) Int. Cl.[7] .......................... C12N 1/14; C12N 15/74; C12Q 1/68

(52) U.S. Cl. .............................. 435/254.2; 435/254.21; 435/6; 435/471

(58) Field of Search .......................... 435/69.1, 320.1, 435/254.11, 254.2, 254.21, 325, 6, 471; 536/23.1

(56) References Cited

U.S. PATENT DOCUMENTS 5,650,283 A * 7/1997 Brandfield et al. .......... 435/7.1

OTHER PUBLICATIONS

Carver et al. J. Bio. Chem. 273(17): 11452–11456, 1997.*
Carver et al. J. Bio. Chem. 269(48):30109–30112, 1994.*
Enan et al. Biochem. Pharmacol. 52:1599–1612, 1996.*
Lucy A. Carver, et al. Ligand–dependent Interaction of the Aryl Hydrocarbon Receptor with a Novel Immunophilin Homolog in Vivo. *The Journal of Biological Chemistry*. 1997. 11452–11456. 17. The American Society for Biochemistry and Molecular Biology, Inc. USA.

Lucy A. Carver, et al. Characterization of the Ah Receptor–associated Protein, ARA9. *The Journal of Biological Chemistry*. 1998. 33580–33587. 273:50. The American Society for Biochemistry and Molecular Biology, Inc. USA.

Lucy A. Carver, et al. The 90–kDa Heat Shock Protein Is Essential for Ah Receptor Signaling in a Yeast Expression System. *The Journal of Biological Chemistry*. 1994. 30109–30112. 269:42. The American Society for Biochemistry and Molecular Biology, Inc. USA.

William K. Chan, et al. Baculovirus Expression of the Ah Receptor Nuclear Translocator. *The Journal of Biological Chemistry*. 1994. 26464–26471. 269:42. The American Society for Biochemistry and Molecular Biology, Inc. USA.

Essam Enan, et al. Identification of c–Src as the Integral Component of the Cytosolic Ah Receptor Complex, Transducing the Signal of 2, 3, 7, 8–Tetrachlorodibenzo–p–dioxin (TCDD) Through the Protein Phosphorylation Pathway. *Biochemical Pharmacology*. 1996. 1599–1612. 52. Elsevier Science Inc.

Giang M., et al. A Novel Cytoplasmic Protein That Interacts with the Ah Receptor, Contains Tetratricopeptide Repeat Motifs, and Augments the Transcriptional Response to 2, 3, 7, 8–Tetrachloridibenzo–p–dioxin. *The Journal of Biological Chemistry*. 1997. 8878–8884. 272:14. The American Society for Biochemistry and Molecular Biology, Inc. USA Brian K. Meyer, et al. Hepatitis B Virus X–Associated Protein 2 Is a Subunit of the Unliganded Aryl Hydrocarbon Receptor Core Complex and Exibits Transcriptional Enhancer Activity. *Molecular and Cellular Biology*. 1998. 978–988. 18:2. The American Society for Microbiology.

Cyrus Vaziri, et al. Expression of the Aryl Hydrocarbon Receptor Is Regulated by Serum and Mitogenic Growth Factors in Murine 3T3 Fibroblasts. *The Journal of Biological Chemistry*. 1996. 25921–25927. 271:42. The American Society for Biochemistry and Molecular Biology, Inc. USA.

* cited by examiner

*Primary Examiner*—Scott D. Priebe
*Assistant Examiner*—Sumesh Kaushal
(74) *Attorney, Agent, or Firm*—Woodcock Washburn LLP

(57) ABSTRACT

Improved cellular assay systems for detecting polycyclic aromatic hydrocarbons, dioxins, PCBs, and other substances which are agonists of the aryl hydrocarbon receptor (AHR) are disclosed. The assays utilize one or more additional cellular proteins involved in the AHR signaling pathway, which improve the sensitivity and maximal responsiveness of the assay systems.

9 Claims, 7 Drawing Sheets

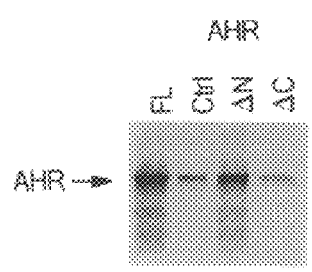 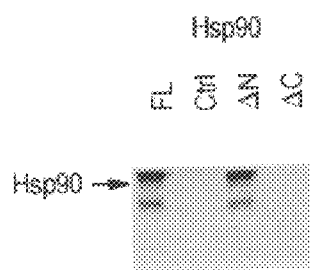 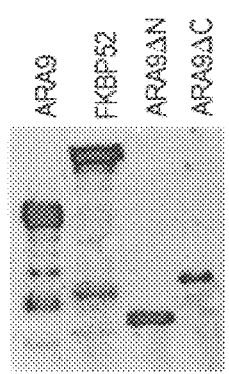
FIG. 2A  FIG. 2B  FIG. 2C
FIG. 2D

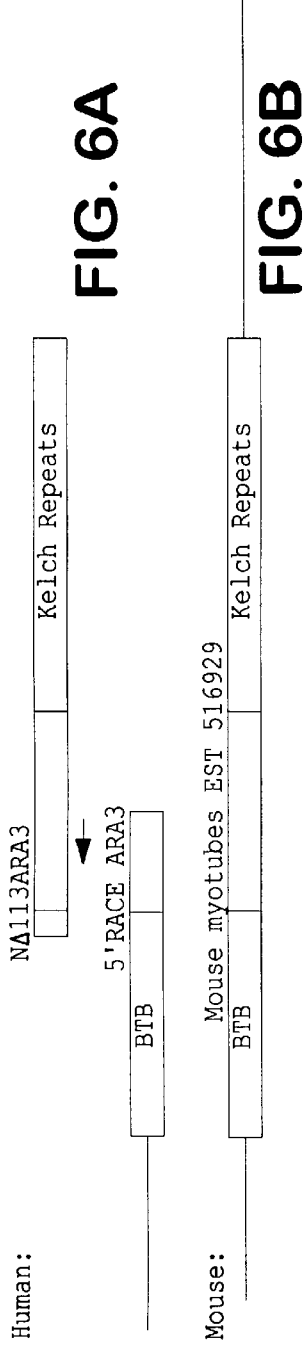

SENSITIVE BIOASSAY FOR DETECTING AGONISTS OF THE ARYL HYDROCARBON RECEPTOR

Pursuant to 35 U.S.C. §202(c), it is acknowledged that the U.S. Government has certain rights in the invention described herein, which was made in part with funds from the National Institutes of Health, Grant Nos. ES05703, CA07175 and ES06883.

FIELD OF THE INVENTION

This invention relates to detection and measurement of environmental pollutants. In particular, the invention provides highly sensitive biological assays for the detection of polycyclic aromatic hydrocarbons, dioxins, PCBs, and other substances which are agonists of the aryl hydrocarbon receptor.

BACKGROUND OF THE INVENTION

Several publications and patents are referenced in this application to describe the state of the art to which the invention pertains. Each of these publications or patents is incorporated by reference herein.

The aryl hydrocarbon receptor (AHR) is a ligand-activated transcription factor that mediates a number of biological responses to planar aromatic hydrocarbons (PAHs). Chemicals which interact with the AHR include a variety of environmental contaminants, such as dioxins, PCBs, PBBs and benzo(a)pyrene, as well as natural products, such as flavones and carbazoles. One of the most potent agonists of the Ah-receptor is 2,3,7,8-tetrachlorodibenzo-p-dioxin (TCDD or "dioxin"). TCDD is the prototype for a large family of highly toxic carcinogenic and teratogenic environmental contaminants (Poland A., Knutson, J. C., Ann. Rev. Pharmacol. Toxicol. 22:517–554, 1982). Members of this family include a number of halogenated dibenzo-p-dioxin, dibenzofuran, and biphenyl isomers, which induce a number of receptor-mediated toxic responses, including a severe wasting syndrome, epidermal hyperplasia and metaplasia, tumor promotion and thymic involution.

The AHR resides primarily in the cytosol, where it is associated with a dimer of the molecular chaperone, Hsp90. Upon binding an agonist, the AHR dissociates from Hsp90, translocates to the nucleus and dimerizes with a structurally related protein, ARNT. This complex interacts with enhancer elements upstream of target promoters and up-regulates the transcription of a variety of xenobiotic metabolizing enzymes (e.g., the Cyt P450 encoded by CYP1A1). The AHR and ARNT are both members of the basic helix-loop-helix-PAS superfamily. The helix-loop-helix domain serves as a dimerization surface for AHR and ARNT and also positions the basic $\alpha$-helix within the major groove of B-DNA to enable specific interactions with target enhancer elements. The PAS domain, a region of ~250 amino acids, functions as a dimerization surface, harbors a repressor region, and also contains regions required for binding agonist and forming interactions with Hsp90.

Recently, other proteins that interact with AHR have been identified. One such "Ah receptor-associated protein" is ARA9 (Carver & Bradfield, J. Biol. Chem. 272: 11452–11456, 1997), also referred to as AIP or XAP2 (Ma & Whitlock, J. Biol. Chem. 272: 8878–8884, 1997; Meyer et al., Mol. Cell. Biol. 18: 978–988, 1998). The 37 kDa ARA9 protein displays structural similarity to the glucocorticoid receptor-associated immunophilin FKBP52. In its amino-terminal half, ARA9 displays sequence identity to a region in FKBP52 known to harbor both peptidylprolyl cis-trans isomerase activity and a high affinity binding site for the immunosuppressant macrolide, FK506. The carboxyl terminal portion of ARA9 has amino acid sequence identity to a region in FKBP52 that harbors multiple TPR motifs (Carver & Bradfield, 1997, supra).

ARA9 has been reported to be involved in the AHR signaling pathway in vivo (Carver & Bradfield, 1997, supra). It has also been reported that overexpression of the protein in mouse hepatoma cells increases the response of that system to the AHR agonist, TCDD, by 2–3 fold.

Another type of protein that has been found to associate with the AHR is the tyrosine kinase encoded by the src oncogene. It has been reported that a c-Src protein kinase specifically associates with the AHR complexed with Hsp90, and upon ligand binding to AHR, the c-Src protein is activated and released from the complex (Enan & Matsamura, Biochem. Pharmacol. 52: 1599–1612, 1996). It has also been reported that tyrosine kinase signaling is needed to induce expression of AHR in 3T3 cells, and that a constitutively active tyrosine kinase, v-Src, is sufficient to confer high levels of AHR expression in the absence of serum (Vaziri et al., J. Biol. Chem. 271: 25921–25927, 1996).

Isolated nucleic acid molecules encoding AHR and ARNT have been used in a recombinant cellular assay system for the detection and measurement of AHR agonists (U.S. Pat. No. 5,650,283 to Bradfield et al., issued Jul. 22, 1997). Cells were engineered to express either ARNT-dependent or ARNT-independent AHR, capable of driving transcription of a reporter gene operably linked to a dioxin-responsive enhancer element (DRE), upon exposure of the cells to an AHR agonist.

The aforementioned cellular assay system provides an effective and rapid means for detecting the presence or amount of an AHR agonist in a test sample. Inasmuch as many such AHR agonists are serious environmental contaminants, the desirability of such an assay is apparent. It would be an advance in the art of environmental monitoring to improve upon such an assay system, e.g., by improving its sensitivity or responsiveness.

SUMMARY OF THE INVENTION

The present invention provides a cellular assay system for AHR agonists that comprises several features and advantages not found in currently available assay systems. These assays incorporate the use of additional proteins involved in the AHR signal transduction pathway, which, alone or in combination, result in an unexpectedly large increase in sensitivity and maximal response of AHR to agonists.

According to one aspect of the invention, a transgenic cell is provided that comprises at least one heterologous vector expressing AHR, ARNT and a protein selected from the group consisting of ARA9, ARA3, Src and any combination thereof. The cell further comprises a reporter gene operably linked to at least one dioxin responsive element, such that the reporter gene expresses a detectable gene product as a result of an AHR agonist binding to the AHR. The transgenic cell may be any appropriate procaryotic or eucaryotic cell. In a preferred embodiment, the transgenic cell is a yeast cell. In another embodiment, the transgenic cell is a vertebrate cell, most preferably a mammalian cell. In another embodiment, the transgenic cell is an insect cell.

According to another aspect of the invention, a transgenic cell is provided that comprises at least one heterologous vector expressing: (i) a chimeric AHR having its dimerization and DNA binding domain replaced with an analogous DNA binding domain from another protein capable of binding a DNA transcriptional activation element and activating transcription of a gene operably linked to the element; (ii) a protein selected from the group consisting of ARA9, ARA3, Src and any combination thereof; and (iii) a reporter gene operably linked to at least one DNA transcriptional activation element, wherein the reporter gene expresses a detectable gene product as a result of an AHR agonist binding to the chimeric AHR. In a preferred embodiment, the transgenic cell is a yeast cell. In another embodiment, it is a vertebrate cell, preferably a mammalian cell. In another embodiment, it is an insect cell.

According to another aspect of the invention, a method is provided for determining if a test compound is an AHR agonist. In one embodiment, the method comprises: (a) providing a transgenic cell comprising at least one heterologous vector expressing AHR, ARNT and a protein selected from the group consisting of ARA9, ARA3, Src and any combination thereof, the cell further comprising a reporter gene operably linked to at least one dioxin responsive element, wherein the reporter gene expresses a detectable gene product as a result of an AHR agonist binding to the AHR; (b) preparing a culture of the transgenic cells; (c) incorporating the test compound into the cell culture under conditions permitting expression of the heterologous vectors, heterodimerization of the AHR and the ARNT, and binding of the heterodimer to the dioxin responsive element; and (d) measuring expression of the reporter gene by detecting the presence or amount, if any, of the detectable gene product and comparing the expression to an equivalent cell culture in which the test compound was not incorporated, an increase in expression of the reporter gene in the culture containing the test compound being indicative that the test compound is an AHR agonist. Another embodiment comprises a similar method, but utilizes a transgenic cell comprising at least one heterologous vector expressing: (i) a chimeric AHR having its dimerization and DNA binding domain replaced with an analogous DNA binding domain from another protein capable of binding a DNA transcriptional activation element and activating transcription of a gene operably linked to the element; (ii) a protein selected from the group consisting of ARA9, ARA3, Src and any combination thereof; and (iii) a reporter gene operably linked to at least one DNA transcriptional activation element, wherein the reporter gene expresses a detectable gene product as a result of an AHR agonist binding to the chimeric AHR.

According to another aspect of the invention, a method for determining if a test compound regulates activity of a protein selected from the group consisting of ARA9, ARA3 and Src is provided. In one embodiment, the method comprises: (a) providing a transgenic cell comprising at least one heterologous vector expressing AHR, ARNT and the protein selected from the group consisting of ARA9, ARA3 and Src, the cell further comprising a reporter gene operably linked to at least one dioxin responsive element, wherein the reporter gene expresses a detectable gene product as a result of an AHR agonist binding to the AHR; (b) preparing a culture of the transgenic cells; (c) incorporating the test compound and an AHR agonist into the cell culture under conditions permitting expression of the heterologous vectors, binding of the AHR agonist to the AHR, heterodimerization of the AHR and the ARNT, and binding of the heterodimer to the dioxin responsive element; and (d) measuring expression of the reporter gene by detecting the presence or amount, if any, of the detectable gene product and comparing the expression to an equivalent cell culture in which the test compound was not incorporated, an increase in expression of the reporter gene in the culture containing the test compound being indicative that the test compound is an AHR agonist. Another embodiment employs a similar method, utilizing a transgenic cell comprising at least one heterologous vector expressing: (i) a chimeric AHR having its dimerization and DNA binding domain replaced with an analogous DNA binding domain from another protein capable of binding a DNA transcriptional activation element and activating transcription of a gene operably linked to the element; (ii) a protein selected from the group consisting of ARA9, ARA3, Src and any combination thereof; and (iii) a reporter gene operably linked to at least one DNA transcriptional activation element, wherein the reporter gene expresses a detectable gene product as a result of an AHR agonist binding to the chimeric AHR.

According to another aspect of the invention, an animal is provided that has enhanced sensitivity to AHR agonists. The animal is modified to overproduce a protein selected from the group consisting of ARA9, ARA3, Src and any combination thereof, which confers the enhanced AHR agonist sensitivity.

According to another aspect of the invention, kits are provided to facilitate performing the above-described assays. In one embodiment, the kits comprise one or more of the DNA constructs encoding AHR, ARNT, ARA9, ARA3, Src and a reporter gene, as described in greater detail herein, along with instructions on how to use the constructs to create transgenic cells or transgenic animals. In another embodiment, the kits comprise aliquots of transgenic cells and instructions for their use. The kits may also comprise, optionally, various reagents for the assays, such as growth media, enzyme substrates for the reporter gene product, and standard solutions for calibrating expression of the reporter gene.

Other features and advantages of the present invention will become apparent from the drawings, detailed description and examples that follow.

BRIEF DESCRIPTION OF THE DRAWINGS

FIG. 2. Characterization of ARA9-AHR interaction and PAS specificity. FIG. 2A. Radiolabeled AHR was incubated in the presence of T7 tagged proteins that had been expressed in bacteria. "FL" is the full length ARA9, "ΔN" is the N-terminal truncation of ARA9, "ΔC" is the C-terminal truncation of ARA9. "Ctrl" is bacteria lysate from untransformed BL21 cells. All complexes were precipitated with T7 tagged agarose. Proteins were separated on 7.5% gel and visualized by autoradiography. FIG. 2B. Radiolabeled Hsp90 was used in a similar assay described in FIG. 2A. FIG. 2C. 4 μg of total extracts used in FIG. 2A were separated on a 10% gel and transferred to nitrocellulose. Western blot analysis was preformed using a T7 antibody conjugated to alkaline phosphatase (Novagen). FIG. 2D. Diagram of ARA9 in which the FKBP12 homology domain is labeled "FKBP" and the domain implicated in binding AHR and Hsp90 is noted by the solid line.

FIG. 3. ARA9 and FKBP52 coimmunoprecipitation of AHR and Hsp90.

FIG. 6. Cloning of ARA3 and amino acid comparison between human and mouse ARA3. FIG. 6A shows a schematic diagram of RACE experiment to clone the 5' end of the human ARA3. The arrow indicates the primer used in the RACE reaction. FIG. 6B shows a schematic diagram of mouse myotube EST 516929 used to clone the mouse ARA3 cDNA. FIG. 6C shows a comparison between the amino acid sequences of the human (SEQ ID NO:3) and mouse (SEQ ID NO:4) ARA3.

DETAILED DESCRIPTION OF THE INVENTION

I. Definitions

Figure 1:
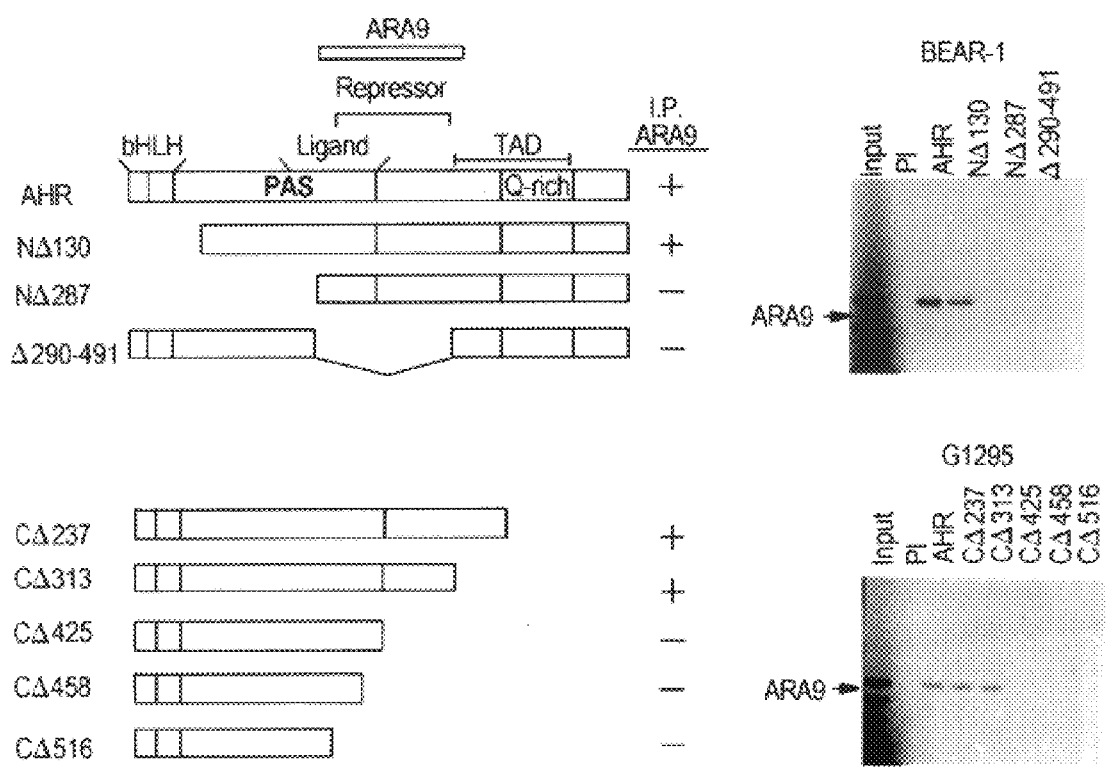
FIG. 1. Coimmunoprecipitation of ARA9 with AHR deletions. Left: Full length AHR and its deletions are depicted on the left. These proteins were combined with full length ARA9 that had been expressed in the presence of $^{35}$S-methionine. All proteins were expressed in reticulocyte lysates. Middle: "IP ARA9," a qualitative interpretation of the immunoprecipitation is provided as plus (efficient immunoprecipitation of ARA9) or minus (no immunoprecipitation). Right: Protein complexes were precipitated with the AHR specific antibodies BEAR-1 (top panel) or G1295 (bottom panel) that had been coupled to Protein-A Sepharose. Preliminary experiments demonstrated that the corresponding deletions were equally immunoprecipitated with these antibodies (data not shown). Proteins were separated on 10% SDS-PAGE, and the co-immunoprecipitated ARA9 was visualized by autoradiography. "Input" is a loading control representing 100% of the radiolabeled ARA9 used in the assay. "PI" is the preimmune control. The ARA9 binding domain deduced from these experiments is described by the bold line.

Various terms relating to the biological molecules and cells of the present invention are used throughout the specifications and claims.

With reference to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule. An isolated nucleic acid molecule inserted into a vector is also sometimes referred to herein as a "recombinant" nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies, the term "immunologically specific" refers to antibodies that bind to one or more epitopes of a protein of interest, but which do not substantially recognize and bind other molecules in a sample containing a mixed population of antigenic biological molecules.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art. For instance, one common formula for calculating the stringency conditions required to achieve hybridization between nucleic acid molecules of a specified sequence homology is set forth below (Sambrook et al., 1989):

$$T_m = 81.5° C. + 16.6 \text{Log}[Na+] + 0.41(\% G+C) - 0.63(\% \text{ formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The term "promoter region" refers to the transcriptional regulatory regions of a gene, which may be found at the 5' or 3' side of the coding region, or within the coding region, or within introns. In the present invention, the use of SV40, TK, Albumin, SP6, T7 gene promoters, among others, is contemplated. Specific promoters for the yeast and mammalian expression systems of the invention are described in greater detail below.

The term "DNA transcriptional activation element" refers to a DNA sequence specifically recognized for binding by a protein characterized as a transcriptional regulator (either activator or suppressor). As one example, the bacterial LexA protein binds to the LexA operator, which is a specific sequence of DNA recognized by the LexA protein for binding and transcriptional activation. The DNA transcriptional activation element is also sometimes referred to herein as a specific "response element" or "responsive element". For instance, the sequence recognized for binding by the AHR/ARNT heterodimer is known as the dioxin response element (DRE).

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

The term "operably linked" means that the regulatory sequences necessary for expression of the coding sequence are placed in the DNA molecule in the appropriate positions relative to the coding sequence so as to enable expression of the coding sequence. This same definition is sometimes applied to the arrangement of transcription units and other transcription control elements (e.g. enhancers) in an expression vector.

II. Description

U.S. Pat. No. 5,650,283 to Bradfield et al. (incorporated by reference herein) describes recombinant cellular yeast and mammalian systems for detecting agonists of the aryl hydrocarbon receptor (AHR), which include environmental pollutants such as polycyclic aromatic hydrocarboons, PCBs and dioxin. Two systems are described; one that is dependent on the activity of the AHR binding partner, ARNT, and one that is independent of ARNT. The present invention is drawn to improvements to those assays, based on the identification of additional proteins that increase the sensitivity or responsiveness of the recombinant systems to AHR agonists. These proteins are sometimes referred to herein as "AHR accessory proteins" or "AHR-associated proteins."

One such AHR-associated protein is the immunophilin, ARA9 (Carver & Bradfield, 1997, supra), identified by the yeast two-hybrid system. ARA9 has been reported to be involved in the AHR signaling pathway in vivo (Carver & Bradfield, 1997, supra). It has also been reported that overexpression of the protein in mouse hepatoma cells increases the response of that system to the AHR agonist, TCDD, by 2–3 fold.

It has been discovered in accordance with the present invention that inclusion of ARA9 in the yeast cellular assay increases the effectiveness of that assay by 10–100 fold, by increasing the sensitivity and maximal responsiveness of the assay to AHR agonists. This discovery was unexpected in view of the minimal increases observed in mouse hepatoma cells overexpressing ARA9. As described in greater detail in Example 1, ARA9 improves the $EC_{50}$ of the yeast expression system by about 10-fold in response to exposure of the cells to AHR agonists, and increases the maximal response up to 3-fold as well.

Another type of protein that has been found to associate with the AHR is the tyrosine kinase encoded by the src oncogene. It has been discovered in accordance with the present invention that inclusion of Src or related tyrosine kinases in the cellular AHR assay improves the effectiveness of the assay by about 3–5 fold. The basis for the improvement observed upon inclusion of Src in the assay is a 3–5 fold increase in maximal responsiveness of the system to an AHR agonist.

Another protein that associates with the AHR is ARA3. ARA3 is a novel protein discovered in accordance with the present invention. A cDNA and deduced amino acid sequence of human ARA3 are set forth herein as SEQ ID NO:1 and SEQ ID NO:3 and a cDNA and deduced amino acid sequence of mouse ARA3 are set forth as SEQ ID NO:2 and SEQ ID NO:4. ARA3 appears to be a mammalian homolog of a family of Drosophila proteins referred to as Kelch proteins. Similar to Src, inclusion of ARA3 in the cellular AHR assay improves the effectiveness of the assay by about 3–5 fold by increasing the maximal responsiveness of the system to AHR agonists.

Thus, the present invention contemplates increasing the sensitivity and/or maximal responsiveness of the cell-based AHR assay to AHR agonists, by including expressible DNA constructs encoding one or more of ARA9, Src and ARA3 in the recombinant cells used in the assay.

The present invention also contemplates novel assays for that affect the aforementioned AHR associated proteins, ARA9, ARA3 and Src. Additionally, these molecules are used to create a model animal system in which the animal is modified to over-express one or more of ARA9, ARA3 or Src, which results in the enhanced sensitivity.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1998) (hereinafter "Ausubel et al.") are used.

III. Preparation of DNA Constructs and Recombinant Cells

Two basic cell assays are contemplated for use in the present invention, though others may also be contemplated as within the scope of the invention. In one system, AHR and ARNT are expressed in the cells, along with one or more of ARA9, ARA3 and Src and a reporter gene controlled by at least one dioxin responsive element (DRE). Stimulation with an AHR agonist causes dimerization of the AHR/ARNT binding pair and subsequent binding of the dimer to the DRE, thereby activating expression of the reporter gene. In an alternative assay, a chimeric AHR is used and ARNT is not expressed in the cells. The chimeric AHR is substituted in the dimerization/DNA binding domain with a sequence encoding a DNA binding domain from another source, which recognizes and binds to a transcriptional activation element without the requirement for heterodimerization with ARNT.

DNA constructs expressing the proteins needed to practice the assays of the invention may be prepared by methods commonly available in the art. Such methods include synthesis from appropriate nucleotide triphosphates or isolation from various biological sources.

Nucleotide sequences of DNA molecules encoding AHR, ARNT, ARA9, Src and, if needed various heat shock proteins, are known in the art. Sequences encoding ARA3 are set forth herein as SEQ ID NO:1 and SEQ ID NO:2, and their respective encoded amino acid sequences as SEQ ID NO:3 and SEQ ID NO:4. Sequence information for human AHR and a chimeric AHR/LexA is set forth in U.S. Pat. No. 5,650,283. Sequence information for ARNT is set forth in Hoffman et al., Science 252: 954–958 (1991; Genbank Accession No. M69238). Sequence information for ARA9 is set forth in Carver & Bradfield, J. Biol. Chem. 272: 11452–11456 (1997). Sequence information for Src is well known in the art.

The availability of such nucleotide sequence information enables preparation of DNA expression constructs of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as the DNA molecules used in the present invention, must be synthesized in stages, due to the size limitations inherent in current oligonucleotide synthetic methods.

Nucleic acid sequences encoding the proteins used in the assays of the invention may be isolated from appropriate biological sources using methods known in the art. In a preferred embodiment, cDNA clones are isolated from libraries of human origin. In an alternative embodiment, genomic clones may be used. Alternatively, cDNA or genomic clones from other species, preferably mammalian species, may be obtained.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable *E. coli* host cell. The DNA constructs maintained in such vectors may thereafter be excised for further cloning into expression vectors for the specific cellular assays or transgenic animals described below.

Chimeric genes such as the AHR chimera described above may be constructed according to commonly available methods, such as those described in Ausbel et al., 1999, supra. For example, the binding domain of the LexA protein can be used. LexA is a protein found in *E. coli* that binds as a dimer to specific DNA sequences upstream of target genes, such as the bacterial gene RecA involved in DNA repair. Since LexA is void of any transcriptional activity, it normally acts as a repressor of transcription until such time that it is cleared and the repression is relieved, allowing the expression of this regulated genes. LexA is often fused to heterologous proteins containing a transactivation domain, thus reconstituting a complex transcription factor that can activate expression of genes located downstream of LexA DNA binding sites (LexA operators). Another protein which can be used is the Gal4 protein. Gal4 normally regulates the expression of genes involved in the pathway for utilizing galactose as a food source. Other DNA binding domains contemplated for use in the present invention include, but are not limited to, those from the tet repressor and LacI.

Expression of the reporter gene is controlled by a suitable promoter and transcription terminator for the cell system being used (e.g., yeast or mammalian in preferred embodiments) and by transcriptional activation element, as defined above. In the AHR/ARNT form of the assay, the transcriptional activation element is one or more dioxin responsive elements (DREs). In the chimeric AHR form of the assay, the transcriptional activation element is the element recognized by the DNA binding domain used in the AHR chimera (e.g., the LexA operator).

Regardless of the cell system, any of a variety of reporter genes can be used. Examples of suitable reporter genes include, but are not limited to: the LacZ gene, encoding β-galactosidase; the neo gene, encoding neomycin phosphotransferase; the CAT gene, encoding chloramphenicol acetyltransferase; dhfr, encoding dihydrofolate reductase; aph IV, encoding hygromycin phosphotransferase; lux, encoding luciferase; uid A, encoding β-glucuronidase, and genes encoding any of a variety of green fluorescent proteins (GFPs) or mutants thereof.

Recombinant cells, preferably yeast or vertebrate cells, can be made to express the DNA constructs encoding AHR and associated proteins described above, along with a reporter gene construct, for use as a sensitive and responsive cellular assay system for measuring the presence or amount of AHR agonists such as dioxin or PCBs. Yeast cells are preferred for use in the present invention, particularly *Saccharomyces cerevisiae* and *Saccharomyces pombe*. Any strain of *S. cerevisiae* or *S. pombe* can be transformed as long as the yeast contains Hsp 90 or a functional homolog thereof (e.g., Hsp 82, Hsc 82).

A yeast expression system comprising either (1) AHR and ARNT or (2) a chimeric AHR such as AHR with a LexA binding domain, along with a suitable reporter plasmid controlled by a responsive element (e.g., DRE, LexA operator), has been fully described in U.S. Pat. No. 5,650,283 to Bradfield et al. and in the published literature (e.g., Carver et al., J. Biol. Chem. 269: 30109–30112, 1994). The yeast expression plasmids and methods described therein form the basis for the yeast cellular assays of the present invention. A cellular assay that also incorporates an expression plasmid for ARA9 is described in Example 1. A cellular assay that incorporates an ARA3 expression plasmid is described in Example 2. Similar expression plasmids are used for expression of Src. In one embodiment of the invention, the yeast expression system comprises the basic AHR or AHR/ARNT and reporter plasmid, along with one DNA construct encoding an accessory protein (e.g., ARA9). In another embodiment, DNA constructs encoding two or more of the three accessory proteins are engineered into the yeast cells.

In addition to yeast cells, vertebrate cells, such as mammalian cells, can be transformed, as described in U.S. Pat. No. 5,650,283. Once construction of the plasmids is completed, they are transfected into mammalian cells, such as COS-1 cells. However, one skilled in the art would recognize that vertebrate cells other than COS-1 cells could be used.

For example, if the commonly-used Gal4 system is employed, a pSG4 vector as described in Sadowski and Ptashne, M. (1989) Nucleic Acids Res. 17: 7539, could be used. The pSG42 vector contains the amino-terminal 147 amino acids of the yeast Gal4 protein under the control of a SV40 promoter, followed by a multiple cloning site that allows in-frame cloning of sequences derived from a second cDNA. Subcloned into this vector is the plasmid pGAHR-N.DELTA.166. Plasmid pGAHRN.DELTA. 166 contains the AHR containing 166 deletions at its amino terminus. The plasmid pGAHRN.DELTA. 166 was generated from the EcoRI, KpnI, BglII, and SacI restriction enzyme fragments of the murine AHR derived from the plasmid pcAHR, and subcloned into the compatible sites of pSG4. Also subcloned into this a fusion protein vector is a plasmid containing ARNT. The plasmid pGARNT can be used. Plasmid pGARNT was constructed by cloning the BamHI fragment from phuARNT (See Dolwick, K. M., Schmidt, J. V., Carver, L. A., Swanson, H. I., and Bradfield, C. A. (1993) Mol. Pharmacol. 44, 911–917). The reporter plasmid can be pG5bCAT which is a chloramphenicol acetyltransferase plasmid containing five USA.sub.G elements upstream of the adenovirus E1B TATA box core promoter. Little, J. W. and Green, M. R. (1989) Nature 338, 39–44. All of these plasmids can be transfected into COS-1 cells.

Though yeast and mammalian cells are preferred for use in the present invention, other expression systems also have been developed for AHR and ARNT, and so would be suitable for use in the present invention. These include cells of other vertebrates, as well as insect cells. For instance, human AHR and ARNT have been expressed in a baculovirus/insect cell expression system (Chan et al., J. Biol. Chem. 269: 26464–26471, 1994).

IV. The Assays and Their Practical Applications

The genetically transformed cells of this invention can be used in highly sensitive and responsive assays to test or detect AHR agonists in environmental samples such as soil, air, and water. The transgenic cells of this invention can also be used in an assay to detect agonists in tissue samples. For instance, a culture of the cells may be prepared, and the samples to be tested can either be incorporated into agar plates or to a liquid media in which the transgenic cells are being propagated. Alternatively, appropriate extraction procedures can be used to prepare the samples for analysis, or purified chemical compounds can be tested. After addition of the analyte, the culture is allowed to grow for approximately 4 to 18 hours to allow for reporter gene expression. The amount of reporter gene expression is determined by measuring the detectable product of the reporter gene. Such measurement varies depending on the reporter gene used, but may include spectrophotometric or fluorimetric measurement of the gene product or its enzymatic activity, or measurement of growth on a selective medium. Such forms of measurement are well known to persons skilled in the art.

The transgenic cells and assays of the invention also can be used to identify substances that regulate or otherwise affect the AHR accessory proteins. For instance, it is anticipated that the immunophilin ARA9, in addition to being involved in AHR signal transduction, is involved in other signal transduction pathways, based in part on its structural similarity to other signal transduction proteins (e.g., FKBP52, involved in T-cell signaling). Accordingly, the cells and assays of the invention can be used to screen for substances that increase or decrease the expression or activity of ARA9. Similarly, ARA3 and Src are anticipated to be involved in one or more signaling pathways, such that the present assays could also be used to screen for compounds that regulate those proteins.

V. AHR Agonist-Sensitive Transgenic Animals

In accordance with another aspect of this invention, transgenic animals may be generated which have altered expression or activity of one or more of the AHR, ARNT or AHR-associated protein-encoding genes described above. The alterations to these genes include modifications, deletions, and substitutions, as well as over-expression due to the engineering of additional gene copies into the animal. Modifications and deletions will render the naturally occurring gene nonfunctional, producing a "knock out" animal. Substitutions of the naturally occurring gene for a gene from a second species results in an animal which produces a gene from the second species. Substitution of the naturally occurring gene for a gene having a mutation results in an animal with a mutated protein. For instance, a transgenic mouse carrying a human gene is generated by direct replacement of the mouse gene with the human gene. These transgenic animals are useful for studies on animal models for human diseases and conditions resulting from exposure to AHR agonists, and for eventual treatment of such disorders.

A transgenic animal that over-expresses a protein involve in AHR signaling, e.g., ARA9, ARA3 or Src, is expected to exhibit enhanced sensitivity to AHR agonists. Such animals are useful for study of AHR signaling and as diagnostic indicators of the presence or amount of a particular AHR agonist. A transgenic animal that is a "knock out" of an AHR accessory protein is also useful for the establishment of a nonhuman model for diseases involving regulation of such proteins.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

A type of target cell for transgene introduction is the embryonal stem cell (ES). ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

VI. Test Kits

The present invention includes test kits to facilitate performing the above-described assays. In one embodiment, the kits comprise one or more of the DNA constructs encoding AHR or chimeric AHR, ARNT, ARA9, ARA3, Src and a reporter gene, along with instructions on how to use the constructs to perform the assays in transgenic cells or transgenic animals containing the constructs. In another embodiment, the kits comprise aliquots of transgenic cells and instructions for their use. The kits may also comprise, optionally, various reagents for the assays, such as growth media, enzyme substrates or other reagents for detecting the report er gene product, and standard solutions for calibrating expression of the reporter gene. One example of a test kit preferred for use in the present invention is a kit that contains a transgenic yeast cell line that expresses either AHR and ARNT, or a chimeric AHR as described above, along with one or more of ARA9, ARA3 and SRC and a reporter gene encoding β-galactosidase, the expression of which controlled by one or more of the appropriate transcriptional activation element (e.g., a DRE for an AHR/ARNT system and a LacZ binding site for an exemplary chimeric AHR). The test kit may further comprise appropriate substrates for detecting β-galactosidase activity (e.g., o-Nitrophenyl-B-D-galactoside) and standards for quantifying the amount of β-galactosidase activity produced by expression of the reporter gene.

The following examples are intended to illustrate embodiments of the invention. They are not intended to limit the scope of the invention in any way.

EXAMPLE 1

Characterization of ARA9

To elucidate the role of ARA9 in AHR signaling, in this example we define the domains within these two proteins that are required for their interaction and also demonstrate that ARA9 expression affects both the potency and efficacy of AHR agonists in the y east S. cerevisiae. Other features of ARA9 are described in detail by Carver et al., J. Biol. Chem. 273: 33580–33587 (1998), incorporated by reference in its entirety.

Materials and Methods

Oligonucleotide Sequences:

SEQ ID NO:5: OL286 CGGGATCCAAGGAATTCAG-CAAGCCACTGC AGG,

SEQ ID NO:6: OL287 CGGGATCCGATGGCTCATCTGCTTCTGTTGCC,

SEQ ID NO:7: OL303 CGGGATCCCAATGGACTC-CAAAGAATCATTA ACTCC,

SEQ ID NO:8: OL304 CGGGATCGGCAGT-CACTTTTGATGAAACAG AG,

SEQ ID NO:9: OL803 CGGAGATCTGAGGCTATGCTTCTGTCTCCACCT,

SEQ ID NO:10: OL813 GCGGAATTCATCTTG-CAGCTGCAGCAGTGGG CTTGG,

SEQ ID NO:11: OL814 CTCTTCGTCTGTCATGGCCCATGG,

SEQ ID NO:12: OL824 GCGGAATTCAGGAAAATG-GCGCTAGCCGGA AGC,

SEQ ID NO:13: OL838 GGTAGATCTGGTAAGGCAGGGCCAAGTGCTCC,

SEQ ID NO:14: OL867 GGTACAGATCTAACGATG-GCGGATATCATCGC ACGCCTC,

SEQ ID NO:15: OL869 GGCGAATTCACGATGTGCT-GCGGTGTTGCACA GATGCG,

SEQ ID NO:16: OL963 GCCGAATTCACGATGGC-CGCCGAGGAGATGA AGGC,

SEQ ID NO:17: OL1066 CGGGAATTCGAGGCTATGCTTCTGTCTCCACCT,

SEQ ID NO:18: OL1151 GCGAATTCGCCACCATG-GCGGATATCATCGCA AGACTCCGG,

SEQ ID NO:19: OL1152 GCGAATTCGCCACCATGCT-GAAGGTGGAGAGCCCTGGC.

Strains and Plasmids: S. cerevisiae strain L40 (MAT a, his3200, trp1-901, leu2-3, 112, ade2, LYS2::(lexAop)$_4$-HIS3, URA3::(lexAop)$_8$-lacZ, gal80) was used in both interaction and pharmacology experiments (Vojtek et al., Cell 74: 205–214, 1993). The GR yeast expression vector, pC7-rGR, was a generous gift of Dr. Didier Picard (Univ. of Geneva, Geneva, Switz.). Plasmid pBTM116 is a 2 μ TRP-marked ADH1 driven expression vector containing the full length E. coli LexA cDNA, followed by a polylinker for generation of fusion proteins (Bartel et al., *Cellular Interactions in Development: A Practical Approach* (D. A. Hartley, ed.), pp.

153–179, IRL Press, Oxford). The plasmid pYPGE2 is a 2 μ, TRP-marked expression vector driven by the PGK1 promoter (Brunelli & Pall, Yeast 9: 1299–1308, 1993). The plasmid pYX242 (Novagen, Madison, Wis.) is a 2 μ, LEU-marked expression plasmid with a TRP1 promoter. The plasmid pGAD424 is a 2 μ, LEU-marked vector for construction of GAL4 transcriptional activation domain fusion proteins (Chien et al., Proc. Natl. Acad. Sci. USA 88: 9578–9582, 1991). The plasmid pBTMAHRNΔ166 (PL703) was constructed by subcloning the EcoRI fragment of pEGAHRNΔ166 (PL700) into the EcoRI site of pBTM116 (Carver et al., 1994, supra). The plasmid pGRNLxC (PL474) is a bacterial expression vector which contains the full length GR cDNA with the DNA binding domain replaced in context with the bacterial LexA DNA binding domain (Godowski et al., Science 241: 812–816, 1988). The plasmid pY2NLxC (PL740) was constructed by amplifying PL474 with the primers OL303 and OL304. The product was cloned into PGEM-Teasy (PL734), and the BamHI fragment was subcloned into the BamHI site of pYPGE2 to yield PL740 (Promega, Madison, Wis.). The plasmids pAHRNΔ130, pAHRNΔ287, pSportAHR, pSportARNT, pSportAHRCΔ237, pSportAHRCΔ313, pSportAHRCΔ425, pSportAHRCΔ458, and pSportAHRCΔ516 have all been previously described (Dolwick et al., Proc. Natl. Acad. Sci. USA 90: 8566–8570, 1993; Carver & Bradfield, 1997, supra; Poland et al., Mol. Pharmacol. 46: 915–921, 1994). The full length ARA9 cDNA was amplified from PL580 (Carver & Bradfield, 1997, supra) with OL824 and OL813 and cloned into the EcoRI site of pSV-SPORT (Gibco/BRL) to make pSportARA9 (PL613). The plasmid pYXARA9 (PL810) was constructed by subcloning the full length ARA9 cDNA from PL613 into the EcoRI site of pYX242. The plasmid pET17b-ARA9 (PL799) was constructed by amplifying PL580 with OL867 and OL838 followed by BglII digestion and the resultant fragment subcloned into the BamHI site of the pET-17b vector (Novagen). The plasmid pET17b-FKBP52 (PL947) was constructed by amplifying FKBP52 from pGEM7Zf-FKBP52 (Lebeau et al., J. Biol. Chem. 267: 4281–4284, 1992) with OL963 and OL1066 and subcloned into the PGEM-T easy vector. The resulting clone was digested with EcoRI and subcloned into the EcoRI site of the pET-17b vector to generate PL947. The carboxy-terminal deletion of ARA9 was constructed by amplifying PL580 with OL1151 and OL814 and cloning of the fragment into PGEM-T easy. The resulting plasmid was digested with EcoRI and the fragment was subcloned into the corresponding site of pET-17b to create pARA9ΔC (PL1005). The amino terminal deletion of ARA9 was created in a similar fashion using OL1152 and OL813 to create pARA9ΔN (PL1004). Plasmids pYXFKBP52 and pGADFKBP52 were designed to express the full length FKBP52 and an FKBP52-GAL4-TAD fusion in yeast. They were constructed by amplifying the FKBP52 cDNA from pGEM7Zf-FKBP52 with OL963 and OL803 and cloning it into PGEM-Teasy. The BamHI fragment was then subcloned into the BamHI site of pYX242 or pGAD424. The plasmid pSportAHRΔ290–491, PL248, was constructed by subcloning the NotI/HindIII fragment of the murine AHR into the corresponding sites of pSportAHRCΔ516.

Co-immnnoprecipitation assays: For AHR domain mapping, proteins were expressed in vitro using the TNT-coupled rabbit reticulocyte lysate system (Promega). In these experiments, the full length ARA9 protein was expressed in the presence of $^{35}$S-methionine for detection by autoradiography. In our hands, this expression system typically produces approximately 1 fmole of $^{35}$S-labeled protein per 5 ul of reaction. Protein complexes were formed by mixing 5 μl of the appropriate in vitro-translated proteins in a 1.5 ml microcentrifuge tube containing 500 ul of MENG buffer (25 mM MOPS, 0.025% NaN$_3$, 1 mM EGTA, 10% (v/v) glycerol, 15 mM NaCl, 1 mM DTT, 0.1% (v/v) NP40, pH 7.5), then incubated for 90 minutes at 4° C. Immunoprecipitations were performed as described previously, using either BEAR-1 or G1295 as the primary antibody (Carver & Bradfield, 1997, supra; Schmidt et al., Proc. Natl. Acad. Sci. USA 93: 6731–6736, 1996).

Bacterial Expression: The ARA9 and FKBP52 proteins tagged with the T7 peptide (PL799, PL1004, PL1005 and PL947) were expressed in BL21(DE3) bacteria (Novagen). The T7 tag is an 11 amino acid peptide, MASMTGGQQMG, that facilitates detection and purification of the recombinant protein using anti-T7 antibodies (Novagen). Saturated cultures were used to inoculate LB growth media supplemented with 0.4 mM IPTG and 100 μg/ml ampicillin. The bacteria were allowed to grow an additional 4 hours at 37° C and pelleted by centrifugation at 5000×g for 5 min. The pellet was resuspended in bind/wash buffer (4.29 mM Na$_2$HPO$_4$, 1.47 mM KH$_2$PO$_4$, 2.7 mM KCl, 0.137 M NaCl, 0.1% (v/v) Tween and 0.002% (w/v) NaN$_3$). The resulting mixture was disrupted using four ×15 second sonic pulses on ice. Insoluble debris was removed by centrifugation at 12,000×g for 20 minutes at 4° C. The supernatant was passed through a 0.45 μM filter and protein concentrations determined by the BCA protein assay (Pierce, Rockford Ill.). The bacterial expression of FKBP52 and ARA9 was confirmed by SDS-PAGE followed by both Coomassie stain and western blot analysis with an anti-T7 peptide antibody (Novagen). Immunoprecipitations of complexes with either AHR- or Hsp90 were performed in MENG buffer as above, using anti-T7 agarose (Novagen). The complexes were then precipitated and analyzed by SDS-PAGE and autoradiography.

Purified ARA9 was prepared from BL21 cells that had been induced by the strategy described above. Following induction, the bacteria were pelleted by centrifugation (5,000×g) and resuspended in MENG buffer. The resulting mixture was disrupted using four ×15 second sonic pulses on ice and cleared by centrifugation (17,000×g). The resulting supernatant was cut with 35–45% ammonium sulfate and centrifuged at 17,000×g. The pellet was washed in ammonium sulfate (45%) and resuspended in MENG buffer. The resulting solution was purified using HPLC on a POROS 10 HQ column using NaCl gradient from 200–800 mM (PerSeptive Biosystems, Cambridge Mass.).

Pharmacology in yeast: AHR dose-response curves were performed in the S. cerevisiae strain L40 as described previously (Carver et al., 1994, supra). Two days after plasmid transformation, the colonies were replica plated on media with various concentrations of βNF spread on the surface. The replica plates were then incubated for two days at 30° C. For each dose of βNF, three colonies were suspended in 100 μl of Z-buffer (60 mM Na$_2$HPO$_4$, 40 mM NaH$_2$PO$_4$, 10 mM KCl, 1 MM MgSO$_4$, 35 mM 2-mercaptoethanol) and cell density was estimated by reading the A$_{600}$. Twenty microliters of the remaining cell suspension was added to 130 μl Z-buffer, 25 μl 0.1%SDS (w/v), 25 μl CHCl$_3$ and disrupted at high speed for 10 sec. Thirty microliters of a 4 mg/ml ONPG solution was added and the mixture incubated for 2–5 min at 30° C. The reaction was stopped by adding 75 μl of 1M NaCO$_3$, the cell debris removed by centrifugation and the A$_{420}$ was determined. Beta-galactosidase units were determined using the following formula (A$_{420}$/(A$_{600}$ of ⅒ dilution of cells×volume of culture×time of incubation))×1,000. To examine expression levels of FKBP52 and ARA9 in yeast, we performed western blot analysis on cell extracts as described previously (Hogenesch et al., J. Biol. Chem. 272: 8581–8593, 1997).
Results:

AHR domains required for ARA9 interaction. In order to map the region of the AHR required for interaction with ARA9, co-immunoprecipitation assays were performed using proteins that had been produced by in vitro translation in reticulocyte lysates. $^{35}$S-labeled ARA9 and a series of deletions of the AHR were mixed and immunoprecipitated with antibodies specific to the basic region (G1295) or the PAS domains (BEAR-1) of the AHR (FIG. 1). We observed that an N-terminal deletion of 130 amino acids (AHRNΔ130) but not 287 residues (AHRNΔ287) was able to form complexes with ARA9. C-terminal deletions of the AHR of up to 313 amino acid (AHRCΔ313) also associated with ARA9, while C-terminal deletions of 425 amino acids (AHRC 425) or greater did not associate with the AHR. This defines the approximate boundaries of the AHR domain required for ARA9 interaction as lying between amino acids 130 and 491. These approximate boundaries are supported by the observation that an AHR construct containing an internal deletion in this region, AHRΔ290–491, does not coimmunoprecipitate ARA9 in parallel experiments.

ARA9 domains required for interaction with AHR and Hsp90: To map the region of ARA9 that is required for interaction with the AHR, two ARA9 mutants that had been T7-tagged were expressed in bacteria and affinity purified. The ARA9ΔC mutant contains the N-terminal amino acids 1–174 corresponding to the FKBP12 homology domain. The ARA9ΔN mutant contains the carboxy-terminal portion of ARA9 (amino acids 154–330) and includes the three TPR domains (FIG. 2). These proteins were tested for their ability to interact with $^{35}$S labeled AHR and Hsp90 in coimmunoprecipitation assays using anti-T7 tag antibodies. In these assays, the C-terminal TPR domains of ARA9 were capable of precipitating both Hsp90 and AHR, while the N-terminal FKBP domain showed no activity above background (FIGS. 2A and 2B). SDS-PAGE analysis indicated that the two mutant ARA9 proteins were expressed to equivalent degrees, arguing against differences in protein expression as an explanation of the differential interaction (FIG. 2C).

Figure 3A:
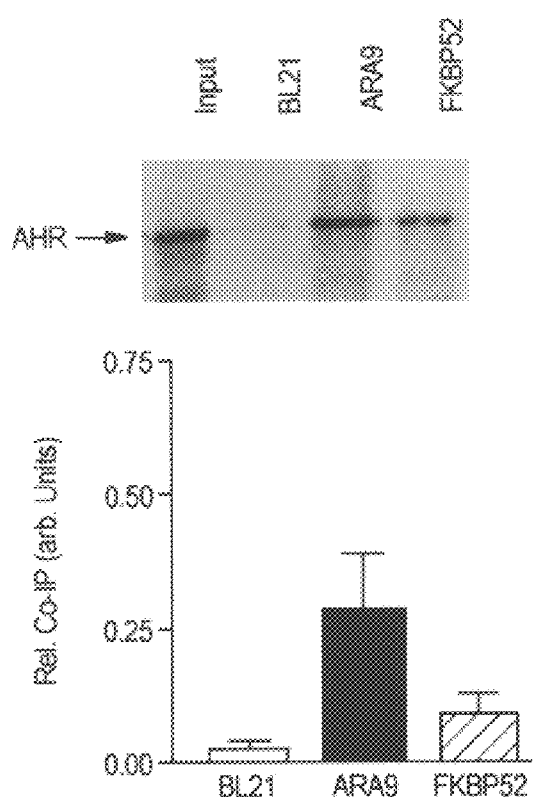
FIG. 3A (Top). AHR was translated in reticulocyte lysates in the presence of $^{35}$S-methionine. Labeled proteins were then incubated in the presence of T7 tagged ARA9, T7 tagged FKBP52 or untransformed BL21 extract and complexes were separated and visualized as above. "Input" lanes represent 25% of total protein (AHR or Hsp90) used in experiments. Bottom: The bands radioactivity present in the AHR or Hsp90 bands was quantified using a phosphoimager to make comparisons of relative coimmunoprecipitation. The bars represent the means from three independent experiments. The error bars indicate the standard error of the mean.
Figure 3B:
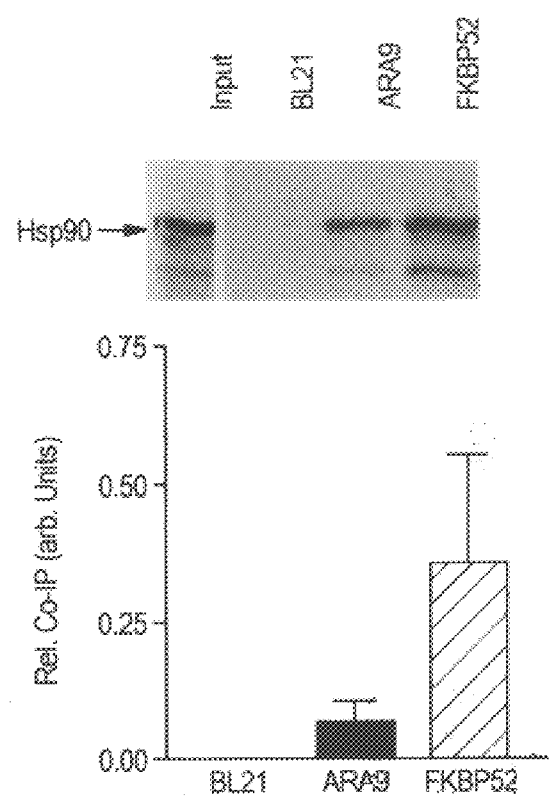
FIG. 3B. Hsp90 was used in a similar experiment described in FIG. 3A.

Specificity of ARA9 for AHR: The structural similarity between ARA9 and FKBP52 led us to compare the relative capacity of these two factors to bind AHR. To determine their relative binding, T7-tagged ARA9 or FKBP52 (expressed in bacteria) were incubated in the presence of $^{35}$S-labeled AHR (expressed in reticulocyte lysates). The AHR-ARA9 or AHR-FKBP52 associations were determined by coimmunoprecipitation with T7-agarose. In this system, ARA9 was approximately four times more efficient at precipitating AHR than was FKBP52 (FIG. 3A). To demonstrate that these results were not due to an inability of FKBP52 to function in this system, or to a lower expression level, we performed a positive control and measured the capacity of ARA9 and FKBP52 to associate with Hsp90. We observed that under the same conditions as those used to assay AHR interactions, FKBP52 exhibited a 4-fold greater capacity to interact with $^{35}$S labeled Hsp90 than did ARA9 (FIG. 3B).

Figure 4:
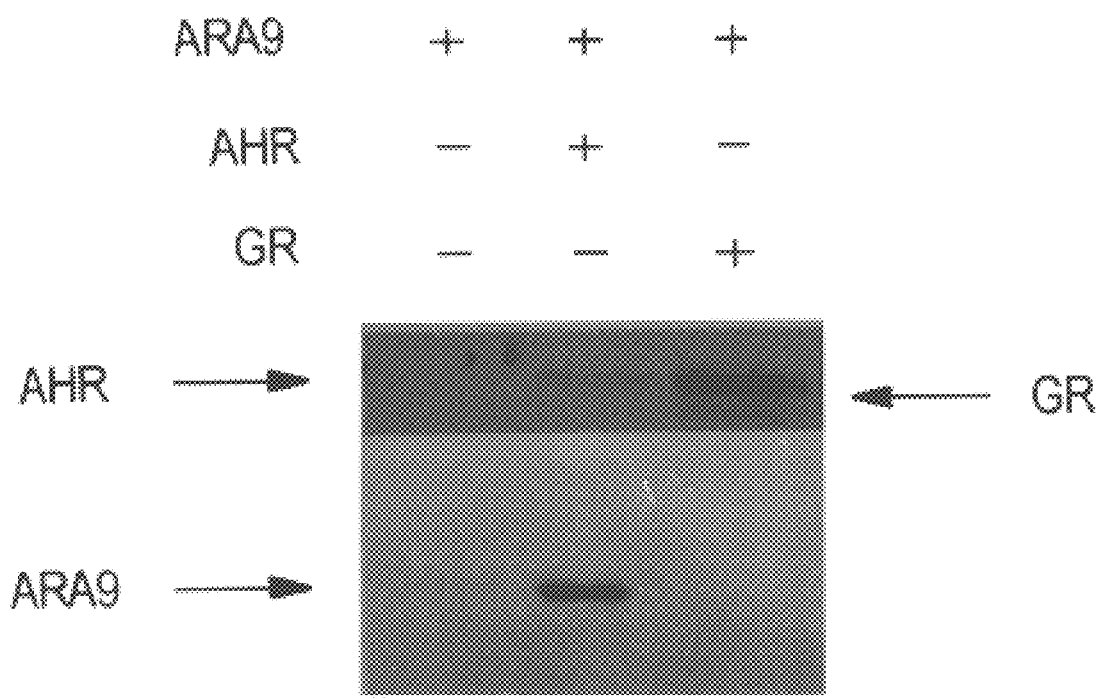
FIG. 4. Effects of AHR and GR on ARA9:Hsp90 interaction. Full length ARA9, AHR and GR were translated in reticulocyte lysates in the presence of $^{35}$S-methionine. The proteins were incubated in the presence of Hsp90 antibody and precipitated with Protein A Sepharose. The proteins were separated by SDS-PAGE and visualized by autoradiography.

In a second experiment, we analyzed the relative capacities of AHR and GR to form higher order complexes that included ARA9 and Hsp90. Our previous work using anti-Hsp90 antibodies demonstrated that ARA9 has a much higher affinity for AHR-Hsp90 complexes than for Hsp90 alone. Therefore, we performed coimmunoprecipitation assays with anti-Hsp90 antibodies to determine if ARA9 also had a higher affinity for GR-Hsp90 complexes. In contrast to AHR, GR was incapable of increasing the ARA9-Hsp90 interaction (FIG. 4).

Figure 5:
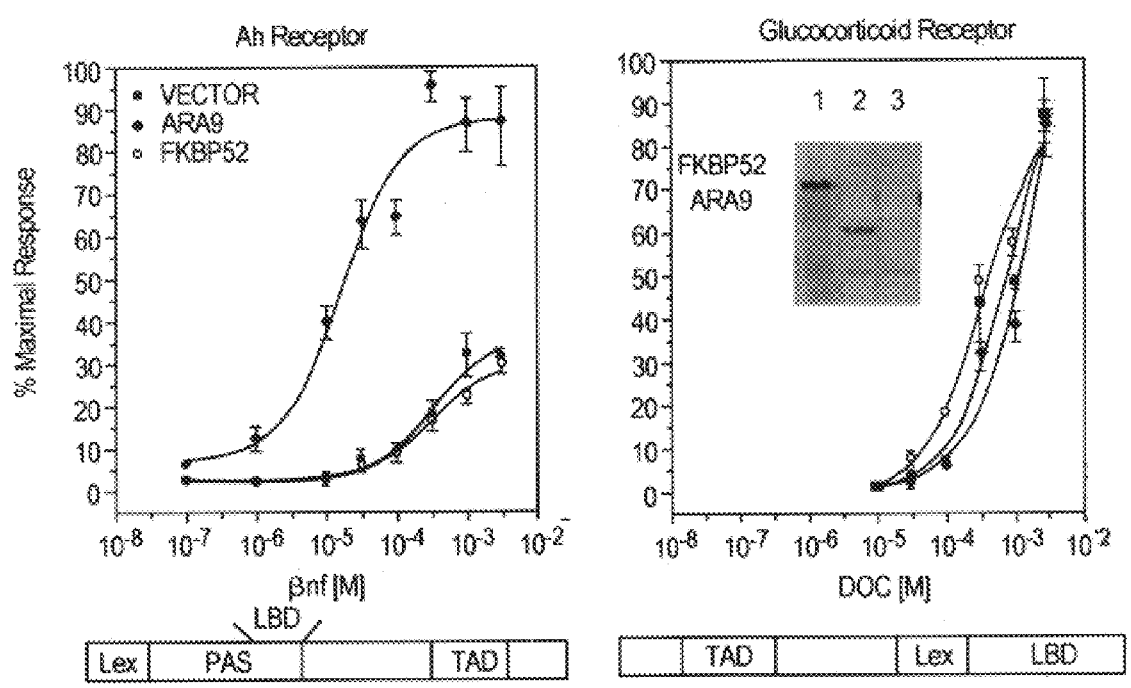
FIG. 5. ARA9 influences AHR signaling in yeast. The yeast strain L40 expressing LexA fusion proteins of the AHR (Left) or GR (right) were transformed with either ARA9 or FKBP52. The yeast transformations were replica plated onto various concentrations of the corresponding ligands (βNF for the AHR and DOC, deoxycorticosterone, for the GR). The yeast were allowed to grow for 2 days and the β-galactosidase activity was measured by the ONPG assay. Values are the average of triplicate determinations (+/− the standard error of the mean). These results are representative of at least two independent experiments. Inset. Western blot analyses of ARA9 and FKBP52 expression in yeast. Lane 1. FKBP52 protein expression in L40 yeast (commercial antibody from Affinity Bioreagents Inc.). Lane 2. ARA9 in L40 yeast. Lane 3. untransformed L40 yeast (1066s, an antibody generated from a amino terminal peptide of ARA9 (64)). Below: Schematics of the AHR and GR constructs. "Lex" is the LexA DNA binding domain. "LBD" is the ligand binding domain. "TAD" is the transcriptionally active domain.

ARA9 enhances ligand responsiveness of AHR: Given the sequence similarities between ARA9 and FKBP52, we asked if either protein could influence AHR signaling in vivo. To this end, we employed a LexA-AHR chimera and a LexA-operator-driven β-galactosidase reporter gene in the yeast S. cerevisiae (Carver et al., 1994, supra). Beta-napthoflavone dose-response curves were constructed for the LexA-AHR in the presence and absence of ARA9 (FIG. 5). Co-expression of ARA9 significantly enhanced the response of AHR to βNF, decreasing the $EC_{50}$ approximately 5-fold when ARA9 was present (FIG. 5. In addition, the maximal response to bNF was increased approximately 2.5 fold in the presence of ARA9 (FIG. 5). In parallel experiments a similar shift in AHR dose-response could not be elicited by FKBP52, nor could either factor alter the response of a GR-LexA chimera to the GR ligand, deoxycorticosterone (FIG. 5). To rule out the possibility that these results were due to lack of expression of either protein in our yeast model system, yeast extracts were subjected to western blot analysis and a high level of both ARA9 and FKBP52 were detected (FIG. 5, inset).
Discussion:

Recently, it has been observed that the AHR-Hsp90 complex contains a 37-kDa protein, ARA9, which displays significant amino acid sequence similarity to FKBP52 AHR (Carver & Bradfield, 1997, supra; Ma & Whitfield, 1997, supra; Meyer et al., 1998, supra). This similarity prompted us to perform a detailed analysis of the AHR-ARA9 interaction. In our first series of experiments, we attempted to define the protein domains required to form the ARA9-Hsp90-AHR complex. To accomplish this, we performed deletion analyses on both ARA9 and AHR and measured the capacity of these mutants to form higher order complexes in vitro. Reticulocyte lysates formed the common milieu for these experiments, since they have been shown to properly fold AHR and are known to contain high levels of Hsp90. In this system, we observed that the TPR domains of ARA9 were both necessary and sufficient to form complexes that contained both AHR and Hsp90. Conversely, the N-terminal half of ARA9 did not interact with either protein. In the reciprocal domain mapping experiments, we observed that ARA9 interacts within the AHR's repressor domain. This region of the AHR has previously been shown to repress receptor activity and harbor the domains required for both Hsp90 and ligand binding.

The domain mapping studies suggest a tertiary complex where ARA9 interacts with Hsp90 through its TPR domains and Hsp90 interacts with AHR through its repressor domain. Given the influence of AHR on ARA9 association), the linear model predicts that AHR directly alters the structure or activity of Hsp90, which in turn allows ARA9 binding. Although this "linear" interaction model has considerable experimental support, it is premature to rule out a more complex model where all proteins are involved in bipartite interactions, i.e., each protein contacts each other protein. For such a model to be correct, the AHR must directly contact ARA9 or additional bridging proteins must exist. Although this has not yet been shown, it may be that direct ARA9-AHR interaction does occur in vivo and simply cannot be detected by the analytical approaches currently in use. If such an interaction does exist, it will be difficult to demonstrate since Hsp90 is required for proper folding of AHR. If the bipartite model was correct, then AHR could have an effect on ARA9 association function through direct contact rather than by influencing the structure of Hsp90.

In this example, we have demonstrated that expression of ARA9 has a functional consequence on AHR signal transduction. Co-expression of ARA9 in a yeast model system significantly increases both the sensitivity and the maximal response of AHR to agonist. Although the molecular basis for this effect in yeast has yet to be determined, it is supported by recent experiments in mammalian cell culture (Ma & Whitlock, 1997, supra; Meyer et al., 1998, supra). Interestingly, the effect of ARA9 on the βNF dose-response curve of AHR is what would be predicted under conditions of increased receptor number. Put in its broadest context, our data are consistent with ARA9 increasing the number of receptors that bind agonist at a given dose or the number of receptors that can progress through a rate-limiting step in signal transduction. Although western blots to approximate AHR expression in yeast extracts do not indicate any influence of ARA9 on total AHR protein levels; these results should not be over-interpreted since it is not yet known what percentage of AHR is properly folded under each condition. In this regard, it is important to note that the data from the GR system suggests that FKBP52 influences GR trafficking to the nucleus and does not necessarily increase total receptor number. A similar mechanism may be at play for ARA9-AHR. EXAMPLE 2

Characterization of ARA3

ARA3 was identified in a modified yeast two-hybrid screen designed to identify novel components of the AHR signaling pathway. The term "ARA3" refers to "AH Receptor Associating protein 3". ARA 3 encodes a novel protein that shows homology to a family of proteins thought to bind actin. ARA3 shows considerable homology (~26% identity) with the Drosophila Kelch protein, a protein essential for ring canal formation at the nurse cell/embryo junction. The Kelch gene encodes a protein with discrete domains consisting of: (1) an amino-terminal BTB (bric-a-brac, tramtrack, broad-complex) domain thought to be involved in protein-protein interactions; (2) an intervening region (IVR) of unknown function, and (3) a carboxy "kelch" repeat domain thought to encode a beta-barrel or beta-propeller structure. The kelch repeat domain is also believed to mediate binding to actin filaments because several kelch repeat proteins associate with actin filaments. An alignment of human and mouse ARA3 amino acid sequences is shown in FIG. 6.

Figure 7A:
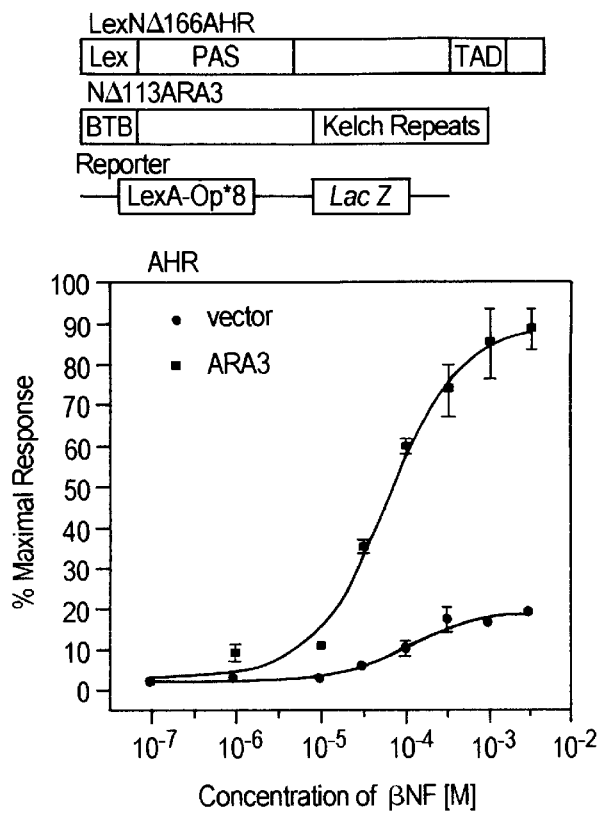
FIG. 7. ARA3 is a specific modifier of the AHR signaling pathway. The top panel for FIG. 7A and FIG. 7B are diagrams representing the constructs expressed and the integrated reporter in L40 yeast. The yeast transformants were replica plated after two days' growth onto increasing concentrations of the appropriate agonists for the particular construct. For all, the β-galactosidase expression was assayed by an o-Nitrophenyl-B-D-galactoside reaction. Values are the mean of triplicate assays ± the standard error.

ARA3 was a candidate for a novel regulator of AHR signaling because of its ligand-dependent association with AHR in the two-hybrid screen. The influence of ARA3 on AHR signaling was investigated to determine modifier status. To accomplish this, an ARA3 cDNA (lacking the heterologous TAD from the two-hybrid clone, TAD-NΔ113ARA3) was expressed with LexA-NΔ166AHR in the L40 strain of yeast with increasing concentrations of β-NF. This slightly truncated ARA3 (NΔ113ARA3) not only increased the maximal response of AHR four-fold but also shifted the curve to the left (see FIG. 7A). These results demonstrated that ARA3 increases the ligand-dependent signaling of AHR.

Figure 7B:
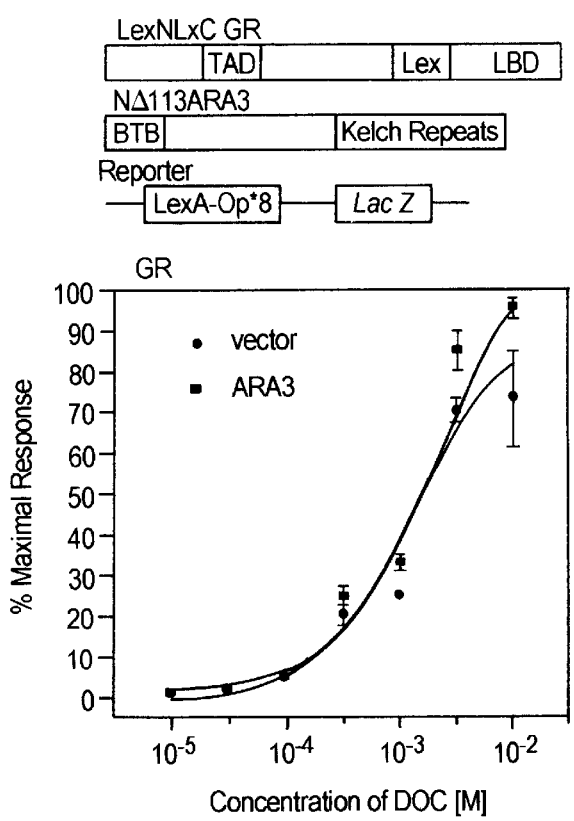

Next, the specificity of ARA3 for the AHR signaling pathway in yeast was examined. As a comparison, we established a glucocorticoid (GR) signaling system in *S. cerevisiae* to serve as a nuclear receptor control for the AHR model system. In this system, GR is expressed as a LexA fusion protein in which the LexA binding domain replaces the GR DNA binding domain. As shown in FIG. 7B, co-expression of ARA3 with NlxC-GR did not alter the signaling profile of GR when using the agonist deoxycorticosterone (DOC) in the L40 strain. These results demonstrate that ARA3 is not ubiquitously affecting other ligand-dependent signaling pathways, and is specific for the AHR pathway in yeast.

The present invention is not limited to the embodiments described and exemplified above, but is capable of variation and modification within the scope of the appended claims.

We claim:

1. An isolated transgenic yeast cell comprising at least one heterologous vector expressing AHR, ARNT and a protein selected from the group consisting of ARA3 and Src and, said cell further comprising a reporter gene operably linked to at least one dioxin responsive element, wherein the reporter gene expresses a detectable gene product as a result of an AHR agonist binding to the AHR, and wherein inclusion of Src results in a three to five fold increase in maximal responsiveness to an AHR agonist.

2. The yeast cell of claim 1, selected from the group consisting of Saccharomyces cerevisiae and Saccharomyces Schizosaccharomyces pombe.

3. The transgenic cell of claim 1, wherein the detectable gene product is β-galactosidase.

4. A transgenic yeast cell comprising at least one heterologous vector expressing:
   i) a chimeric AHR having its dimerization and DNA binding domain replaced with a DNA binding domain from another protein capable of binding a DNA transcriptional activation element and activating transcription of a gene operably linked to the element;
   ii) a protein selected from the group consisting of ARA3, Src and any combination thereof; and
   iii) a reporter gene operably linked to at least one said DNA transcriptional activation element, wherein the reporter gene expresses a detectable gene product as a result of an AHR agonist binding to the chimeric AHR, wherein inclusion of Src results in a three to five fold increase in maximal responsiveness to an AHR agonist.

5. The yeast cell of claim 4, selected from the group consisting of Saccharomyces cerevisiae and Saccharomyces Schizosaccharomyces pombe.

6. The transgenic cell of claim 4, wherein the chimeric AHR comprises a DNA binding domain from a LexA protein and the transcriptional activation element is a LexA operator.

7. The transgenic cell of claim 4, wherein the detectable gene product is β-galactosidase.

8. An isolated transgenic yeast cell comprising at least one heterologous vector expressing AHR, ARNT and ARA3 and, optionally, a protein selected from the group consisting of ARA9, Src, said cell further comprising a reporter gene operably linked to at least one dioxin responsive element, wherein the reporter gene expresses a detectable gene product as a result of an AHR agonist binding to the AHR.

9. A transgenic yeast cell comprising at least one heterologous vector expressing:
   i) a chimeric AHR having its dimerization and DNA binding domain replaced with a DNA binding domain from another protein capable of binding a DNA transcriptional activation element and activating transcription of a gene operably linked to the element;
   ii) ARA3;
   iii) optionally, a protein selected from the group consisting of ARA9, Src and a combination thereof; and
   iv) a reporter gene operably linked to at least one said DNA transcriptional activation element, wherein the reporter gene expresses a detectable gene product as a result of an AHR agonist binding to the chimeric AHR.

* * * * *

SEQUENCE LISTING

<160> NUMBER OF SEQ ID NOS: 19

<210> SEQ ID NO 1
<211> LENGTH: 1929
<212> TYPE: DNA
<213> ORGANISM: Homo sapiens
<220> FEATURE:
<221> NAME/KEY: misc_feature
<223> OTHER INFORMATION: /note = "ARA3"

<400> SEQUENCE: 1

```
atgattccca atggatattt gatgtttgag gatgaaaatt ttattgagtc t tctgttgcc      60 aaattaaatg ccctgaggaa aagtggccag ttctgtgatg ttcgacttca g gtctgtggc     120 catgaaatgt tagcacacag agcagtgcta gcttgctgca gtccctattt a tttgaaatc     180 tttaatagtg atagtgatcc tcatggaatt tctcacgtta aatttgatga t ctcaatcca    240 gaagctgttg aagtcttgtt gaattatgcc tacactgctc agttgaaagc a gataaggaa    300 ttggtaaaag atgtttattc tgcagcaaaa aagctgaaga tggatcgagt a aagcaggtt    360 tgtggtgatt atttactgtc tagaatggat gttaccagct gcatctctta c cgaaatttt    420 gcaagttgta tgggagactc ccgtttgttg aataaggttg atgcttatat t caggagcat    480
```

```
ttgttacaaa tttctgaaga ggaggagttt cttaagcttc caaggctaaa g ttggaggta      540
atgcttgaag ataatgtttg cttgcccagc aatggcaaat tatatacaaa g gtaatcaac      600
tgggtgcagc gtagcatctg ggagaatgga gacagtctgg aagagctgat g gaagaggtt      660
caaaccttgt actactcagc tgatcacaag ctgcttgatg gaacctact a gatggacag       720
gctgaggtgt ttggcagtga tgatgaccac attcagtttg tgcagaaaaa g ccaccacgt      780
gagaatggcc ataagcagat aagtagcagt tcaactggat gtctctcttc t ccaaatgct      840
acagtacaaa gccctaagca tgagtggaaa tcgttgctt cagaaaagac t tcaaataac       900
acttacttgt gcctggctgt gctggatggt atattctgtg tcatttttct t catgggaga      960
aacagcccac agagctcacc aacaagtact ccaaaactaa gtaagagttt a gctttgag      1020
atgcaacaag atgagctaat cgaaaagccc atgtctccta tgcagtacgc a cgatctggt     1080
ctgggaacag cagagatgaa tggcaaactc atagctgcag gtggctataa c agagaggaa     1140
tgtcttcgaa cagtcgaatg ctataatcca catacagatc actggtcctt t cttgctccc     1200
atgagaacac caagagcccg atttcaaatg gctgtactca tgggccagct c tatgtggtg     1260
ggtggatcaa atggccactc agatgacctg agttgtggag agatgtatga t tcaaacata     1320
gatgactgga ttcctgttcc agaattgaga actaaccgtt gtaatgcagg a gtgtgtgct     1380
ctgaatggaa agttatacat cgttggtggc tctgatccat atggtcaaaa a ggactgaaa     1440
aattgtgatg tatttgatcc tgtaacaaag ttgtggacaa gctgtgcccc t cttaacatt     1500
cggagacacc agtctgcagt ctgtgagctt ggtggttatt tgtacataat c ggaggtgca     1560
gaatcttgga attgtctgaa cacagtagaa cgatacaatc ctgaaaataa t acctggact     1620
taattgcac ccatgaatgt ggctaggcga ggagctggag tggctgttct t aatggaaaa     1680
ctgtttgtat gtggtggctt tgatggttct catgccatca gttgtgtgga a atgcatgat     1740
ccaactagaa atgaatggaa gatgatggga acatgacttc accaaggag c aatgctggg     1800
attgcaactg tagggaacac catttatgca gtgggaggat tcgatggcaa t gaatttctg     1860
aatacggtgg aagtctataa ccttgagtca aatgaatgga gcccctatac a agattttc     1920
cagttttaa                                                               1929
```

<210> SEQ ID NO 2
<211> LENGTH: 1929
<212> TYPE: DNA
<213> ORGANISM: Mus musculus
<220> FEATURE:
<221> NAME/KEY: misc_feature
<223> OTHER INFORMATION: /note = "ARA3"

<400> SEQUENCE: 2

```
atgattccca atggatattt gatgtttgaa gatgaaaatt ttattgaatc a tctgttgcc       60
aaattaaatg ccttgaggaa gagtgggcag ttctgtgatg ttcgacttca g gtctgtggc      120
catgagatgc tagcacacag ggcagtcctg gcttgctgta gccccatctc t tttgaaatc      180
ttcaatagtg acagtgaccc tcatggagtt tctcatgtga agttggatga t ctcaatcca      240
gaagctgttg aagtcttgct gaattatgca tacacggctc agttgaaagc t gataaggaa      300
ttagtaaaag atgtttattc tgcagccaag aagctgaaga tggaccgagt c aagcaggtc      360
tgcggagatt atttactatc tagaatggat gttactagct gcatctctta c cgaaattt       420
gcaagttgta tgggagactc ccgtttgttg aataaagttg acgcttatat t caggagcat      480
ttgttacaaa tttcagaaga ggaggaattt cttaagcttc cgagactaaa g ttggaggta      540
```

-continued

```
atgcttgaag ataatgtgtg cttgcccagc aatggcaagt tgtatacaaa g gtaatcaac        600
tgggtgcagc gtagcatctg ggagaatgga gacagcctgg aggagctcat g gaagaggtt        660
caaaccttgt actactcagc tgatcacaag ctgcttgatg ggaacccact a gatggacag        720
gctgaggtgt ttggcagtga tgatgaccac attcagtttg tgcagaaaaa g ccaccccgt        780
gagaatggcc ataagcagat aagtggcagt tccactggat gtctctcttc t ccaaatgct        840
tcaatgcaaa gccctaagca tgagtggaaa tcgttgcttc agaaaagac t tcaaataac         900
acttacttgt gcctggctgt gctggacagt acattctgtg tcattttcct t catgggcgg        960
aacagtccac agagctcacc aacaagtact ccaaaactga gcaagagttt a agcttcgag       1020
atgcaaccag atgagcttct agaaaagccc atgtctccca tgcagtacgc a cggtctgga       1080
ctagggacag cagagatgaa tggcaaactc atagctgcag gtggttataa c agagaggaa       1140
tgtcttcgaa cagttgaatg ctatgatcca catacagatc actggtcctt c cttgctccc       1200
atgagaacac caagagcccg ctttcaaatg gctgtgctga tgggacagct c tatgtggtg       1260
ggtggatcaa atggacactc agatgacctg agttgtggag aaatgtatga t ccaaacatt       1320
gatgactgga cccctgttcc agagctgaga accaaccgtt gtaatgcagg a gtgtgtgct       1380
ctgaatggga aattgtacat tgttggtggc tctgatccat atggtcaaaa g ggcctgaaa       1440
aattgtgatg tatttgatcc tgtaacgaag tcatggacaa gctgtgctcc t cttaacatt       1500
cgtcgacacc agtctgcagt ttgtgaactt ggtggttatt tgtatataat t ggaggtgca       1560
gaatcttgga attgtctgaa cacagtagaa cgatacaatc ctgaaaacaa c acctggact       1620
ttaattgcac ccatgaatgt ggcgaggcga ggggctggag tcgctgtgct t gatggaaaa       1680
ctgtttgtag gtggtggctt tgatggttct cacgccatca gttgtgtgga g atgtatgat       1740
ccaactagaa atgaatggaa gatgatggga aatatgactt caccaaggag c aatgctggg       1800
atcacaactg tagggaatac catttatgca gtgggaggat tcgatggcaa t gagtttctg       1860
aatactgtgg aagtctacaa ccctcagtca aatgagtgga gcccttacac a aagattttc       1920
cagttttaa                                                                 1929
```

<210> SEQ ID NO 3
<211> LENGTH: 642
<212> TYPE: PRT
<213> ORGANISM: Homo sapiens
<220> FEATURE:
<221> NAME/KEY: misc_feature
<223> OTHER INFORMATION: /note = "ARA3"

<400> SEQUENCE: 3

```
Met Ile Pro Asn Gly Tyr Leu Met Phe Glu A sp Glu Asn Phe Ile Glu
1               5                   10                  15

Ser Ser Val Ala Lys Leu Asn Ala Leu Arg L ys Ser Gly Gln Phe Cys
            20                  25                  30

Asp Val Arg Leu Gln Val Cys Gly His Glu M et Leu Ala His Arg Ala
        35                  40                  45

Val Leu Ala Cys Cys Ser Pro Tyr Leu Phe G lu Ile Phe Asn Ser Asp
    50                  55                  60

Ser Asp Pro His Gly Ile Ser His Val Lys P he Asp Asp Leu Asn Pro
65                  70                  75                  80

Glu Ala Val Glu Val Leu Leu Asn Tyr Ala T yr Thr Ala Gln Leu Lys
                85                  90                  95

Ala Asp Lys Glu Leu Val Lys Asp Val Tyr S er Ala Ala Lys Lys Leu
```

-continued

```
                    100                 105                 110
Lys Met Asp Arg Val Lys Gln Val Cys Gly Asp Tyr Leu Leu Ser Arg
                115                 120                 125
Met Asp Val Thr Ser Cys Ile Ser Tyr Arg Asn Phe Ala Ser Cys Met
            130                 135                 140
Gly Asp Ser Arg Leu Leu Asn Lys Val Asp Ala Tyr Ile Gln Glu His
145                 150                 155                 160
Leu Leu Gln Ile Ser Glu Glu Glu Phe Leu Lys Leu Pro Arg Leu
                165                 170                 175
Lys Leu Glu Val Met Leu Glu Asp Asn Val Cys Leu Pro Ser Asn Gly
                180                 185                 190
Lys Leu Tyr Thr Lys Val Ile Asn Trp Val Gln Arg Ser Ile Trp Glu
                195                 200                 205
Asn Gly Asp Ser Leu Glu Glu Leu Met Glu Glu Val Gln Thr Leu Tyr
210                 215                 220
Tyr Ser Ala Asp His Lys Leu Leu Asp Gly Asn Leu Leu Asp Gly Gln
225                 230                 235                 240
Ala Glu Val Phe Gly Ser Asp Asp His Ile Gln Phe Val Gln Lys
                245                 250                 255
Lys Pro Pro Arg Glu Asn Gly His Lys Gln Ile Ser Ser Ser Ser Thr
                260                 265                 270
Gly Cys Leu Ser Ser Pro Asn Ala Thr Val Gln Ser Pro Lys His Glu
                275                 280                 285
Trp Lys Ile Val Ala Ser Glu Lys Thr Ser Asn Asn Thr Tyr Leu Cys
                290                 295                 300
Leu Ala Val Leu Asp Gly Ile Phe Cys Val Ile Phe Leu His Gly Arg
305                 310                 315                 320
Asn Ser Pro Gln Ser Ser Pro Thr Ser Thr Pro Lys Leu Ser Lys Ser
                325                 330                 335
Leu Ser Phe Glu Met Gln Gln Asp Glu Leu Ile Glu Lys Pro Met Ser
                340                 345                 350
Pro Met Gln Tyr Ala Arg Ser Gly Leu Gly Thr Ala Glu Met Asn Gly
                355                 360                 365
Lys Leu Ile Ala Ala Gly Gly Tyr Asn Arg Glu Glu Cys Leu Arg Thr
                370                 375                 380
Val Glu Cys Tyr Asn Pro His Thr Asp His Trp Ser Phe Leu Ala Pro
385                 390                 395                 400
Met Arg Thr Pro Arg Ala Arg Phe Gln Met Ala Val Leu Met Gly Gln
                405                 410                 415
Leu Tyr Val Val Gly Gly Ser Asn Gly His Ser Asp Asp Leu Ser Cys
                420                 425                 430
Gly Glu Met Tyr Asp Ser Asn Ile Asp Asp Trp Ile Pro Val Pro Glu
                435                 440                 445
Leu Arg Thr Asn Arg Cys Asn Ala Gly Val Cys Ala Leu Asn Gly Lys
                450                 455                 460
Leu Tyr Ile Val Gly Gly Ser Asp Pro Tyr Gly Gln Lys Gly Leu Lys
465                 470                 475                 480
Asn Cys Asp Val Phe Asp Pro Val Thr Lys Leu Trp Thr Ser Cys Ala
                485                 490                 495
Pro Leu Asn Ile Arg Arg His Gln Ser Ala Val Cys Glu Leu Gly Gly
                500                 505                 510
Tyr Leu Tyr Ile Ile Gly Gly Ala Glu Ser Trp Asn Cys Leu Asn Thr
                515                 520                 525
```

-continued

```
Val Glu Arg Tyr Asn Pro Glu Asn Asn Thr Trp Thr Leu Ile Ala Pro
    530                 535                 540

Met Asn Val Ala Arg Arg Gly Ala Gly Val Ala Val Leu Asn Gly Lys
545                 550                 555                 560

Leu Phe Val Cys Gly Gly Phe Asp Gly Ser His Ala Ile Ser Cys Val
                565                 570                 575

Glu Met His Asp Pro Thr Arg Asn Glu Trp Lys Met Met Gly Asn Met
            580                 585                 590

Thr Ser Pro Arg Ser Asn Ala Gly Ile Ala Thr Val Gly Asn Thr Ile
        595                 600                 605

Tyr Ala Val Gly Gly Phe Asp Gly Asn Glu Phe Leu Asn Thr Val Glu
    610                 615                 620

Val Tyr Asn Leu Glu Ser Asn Glu Trp Ser Pro Tyr Thr Lys Ile Phe
625                 630                 635                 640

Gln Phe
```

<210> SEQ ID NO 4
<211> LENGTH: 642
<212> TYPE: PRT
<213> ORGANISM: Mus musculus
<220> FEATURE:
<221> NAME/KEY: misc_feature
<223> OTHER INFORMATION: /note = "ARA3"

<400> SEQUENCE: 4

```
Met Ile Pro Asn Gly Tyr Leu Met Phe Glu Asp Glu Asn Phe Ile Glu
1               5                   10                  15

Ser Ser Val Ala Lys Leu Asn Ala Leu Arg Lys Ser Gly Gln Phe Cys
            20                  25                  30

Asp Val Arg Leu Gln Val Cys Gly His Glu Met Leu Ala His Arg Ala
        35                  40                  45

Val Leu Ala Cys Cys Ser Pro Tyr Leu Phe Glu Ile Phe Asn Ser Asp
    50                  55                  60

Ser Asp Pro His Gly Ile Ser His Val Lys Phe Asp Asp Leu Asn Pro
65                  70                  75                  80

Glu Ala Val Glu Val Leu Leu Asn Tyr Ala Tyr Thr Ala Gln Leu Lys
                85                  90                  95

Ala Asp Lys Glu Leu Val Lys Asp Val Tyr Ser Ala Ala Lys Lys Leu
            100                 105                 110

Lys Met Asp Arg Val Lys Gln Val Cys Gly Asp Tyr Leu Leu Ser Arg
        115                 120                 125

Met Asp Val Thr Ser Cys Ile Ser Tyr Arg Asn Phe Ala Ser Cys Met
    130                 135                 140

Gly Asp Ser Arg Leu Leu Asn Lys Val Asp Ala Tyr Ile Gln Glu His
145                 150                 155                 160

Leu Leu Gln Ile Ser Glu Glu Glu Phe Leu Lys Leu Pro Arg Leu
                165                 170                 175

Lys Leu Glu Val Met Leu Glu Asp Asn Val Cys Leu Pro Ser Asn Gly
            180                 185                 190

Lys Leu Tyr Thr Lys Val Ile Asn Trp Val Gln Arg Ser Ile Trp Glu
        195                 200                 205

Asn Gly Asp Ser Leu Glu Glu Leu Met Glu Glu Val Gln Thr Leu Tyr
    210                 215                 220

Tyr Ser Ala Asp His Lys Leu Leu Asp Gly Asn Leu Leu Asp Gly Gln
225                 230                 235                 240
```

```
Ala Glu Val Phe Gly Ser Asp Asp His Ile Gln Phe Val Gln Lys
                245                 250                 255

Lys Pro Pro Arg Glu Asn Gly His Lys Gln Ile Ser Ser Ser Thr
            260                 265                 270

Gly Cys Leu Ser Ser Pro Asn Ala Thr Val Gln Ser Pro Lys His Glu
            275                 280                 285

Trp Lys Ile Val Ala Ser Glu Lys Thr Ser Asn Asn Thr Tyr Leu Cys
    290                 295                 300

Leu Ala Val Leu Asp Gly Ile Phe Cys Val Ile Phe Leu His Gly Arg
305                 310                 315                 320

Asn Ser Pro Gln Ser Ser Pro Thr Ser Thr Pro Lys Leu Ser Lys Ser
                325                 330                 335

Leu Ser Phe Glu Met Gln Gln Asp Glu Leu Ile Glu Lys Pro Met Ser
                340                 345                 350

Pro Met Gln Tyr Ala Arg Ser Gly Leu Gly Thr Ala Glu Met Asn Gly
                355                 360                 365

Lys Leu Ile Ala Ala Gly Gly Tyr Asn Arg Glu Glu Cys Leu Arg Thr
370                 375                 380

Val Glu Cys Tyr Asn Pro His Thr Asp His Trp Ser Phe Leu Ala Pro
385                 390                 395                 400

Met Arg Thr Pro Arg Ala Arg Phe Gln Met Ala Val Leu Met Gly Gln
                405                 410                 415

Leu Tyr Val Val Gly Gly Ser Asn Gly His Ser Asp Asp Leu Ser Cys
                420                 425                 430

Gly Glu Met Tyr Asp Ser Asn Ile Asp Asp Trp Ile Pro Val Pro Glu
                435                 440                 445

Leu Arg Thr Asn Arg Cys Asn Ala Gly Val Cys Ala Leu Asn Gly Lys
        450                 455                 460

Leu Tyr Ile Val Gly Gly Ser Asp Pro Tyr Gly Gln Lys Gly Leu Lys
465                 470                 475                 480

Asn Cys Asp Val Phe Asp Pro Val Thr Lys Leu Trp Thr Ser Cys Ala
                485                 490                 495

Pro Leu Asn Ile Arg Arg His Gln Ser Ala Val Cys Glu Leu Gly Gly
                500                 505                 510

Tyr Leu Tyr Ile Ile Gly Gly Ala Glu Ser Trp Asn Cys Leu Asn Thr
        515                 520                 525

Val Glu Arg Tyr Asn Pro Glu Asn Asn Thr Trp Thr Leu Ile Ala Pro
            530                 535                 540

Met Asn Val Ala Arg Arg Gly Ala Gly Val Ala Val Leu Asn Gly Lys
545                 550                 555                 560

Leu Phe Val Cys Gly Gly Phe Asp Gly Ser His Ala Ile Ser Cys Val
                565                 570                 575

Glu Met His Asp Pro Thr Arg Asn Glu Trp Lys Met Met Gly Asn Met
            580                 585                 590

Thr Ser Pro Arg Ser Asn Ala Gly Ile Ala Thr Val Gly Asn Thr Ile
            595                 600                 605

Tyr Ala Val Gly Gly Phe Asp Gly Asn Glu Phe Leu Asn Thr Val Glu
            610                 615                 620

Val Tyr Asn Leu Glu Ser Asn Glu Trp Ser Pro Tyr Thr Lys Ile Phe
625                 630                 635                 640

Gln Phe
```

```
<210> SEQ ID NO 5
<211> LENGTH: 33
<212> TYPE: DNA
<213> ORGANISM: Artificial Sequence
<220> FEATURE:
<223> OTHER INFORMATION: Synthetic construct

<400> SEQUENCE: 5
cgggatccaa ggaattcagc aagccactgc agg                              33

<210> SEQ ID NO 6
<211> LENGTH: 32
<212> TYPE: DNA
<213> ORGANISM: Artificial Sequence
<220> FEATURE:
<223> OTHER INFORMATION: Synthetic construct

<400> SEQUENCE: 6
cgggatccga tggctcatct gcttctgttg cc                               32

<210> SEQ ID NO 7
<211> LENGTH: 36
<212> TYPE: DNA
<213> ORGANISM: Artificial Sequence
<220> FEATURE:
<223> OTHER INFORMATION: Synthetic construct

<400> SEQUENCE: 7
cgggatccca atggactcca agaatcatt aactcc                            36

<210> SEQ ID NO 8
<211> LENGTH: 33
<212> TYPE: DNA
<213> ORGANISM: Artificial Sequence
<220> FEATURE:
<223> OTHER INFORMATION: Synthetic construct

<400> SEQUENCE: 8
cgggatcggc agtcactttt gatgaaacag aag                              33

<210> SEQ ID NO 9
<211> LENGTH: 33
<212> TYPE: DNA
<213> ORGANISM: Artificial Sequence
<220> FEATURE:
<223> OTHER INFORMATION: Synthetic construct

<400> SEQUENCE: 9
cggagatctg aggctatgct tctgtctcca cct                              33

<210> SEQ ID NO 10
<211> LENGTH: 36
<212> TYPE: DNA
<213> ORGANISM: Artificial Sequence
<220> FEATURE:
<223> OTHER INFORMATION: Synthetic construct

<400> SEQUENCE: 10
gcggaattca tcttgcagct gcagcagtgg gcttgg                           36

<210> SEQ ID NO 11
<211> LENGTH: 24
<212> TYPE: DNA
<213> ORGANISM: Artificial Sequence
<220> FEATURE:
<223> OTHER INFORMATION: Synthetic construct
```

<400> SEQUENCE: 11
ctcttcgtct gtcatggccc atgg                                    24

<210> SEQ ID NO 12
<211> LENGTH: 33
<212> TYPE: DNA
<213> ORGANISM: Artificial Sequence
<220> FEATURE:
<223> OTHER INFORMATION: Synthetic construct

<400> SEQUENCE: 12
gcggaattca ggaaaatggc gctagccgga agc                          33

<210> SEQ ID NO 13
<211> LENGTH: 32
<212> TYPE: DNA
<213> ORGANISM: Artificial Sequence
<220> FEATURE:
<223> OTHER INFORMATION: Synthetic construct

<400> SEQUENCE: 13
ggtagatctg gtaaggcagg gccaagtgct cc                           32

<210> SEQ ID NO 14
<211> LENGTH: 39
<212> TYPE: DNA
<213> ORGANISM: Artificial Sequence
<220> FEATURE:
<223> OTHER INFORMATION: Synthetic construct

<400> SEQUENCE: 14
ggtacagatc taacgatggc ggatatcatc gcacgcctc                    39

<210> SEQ ID NO 15
<211> LENGTH: 38
<212> TYPE: DNA
<213> ORGANISM: Artificial Sequence
<220> FEATURE:
<223> OTHER INFORMATION: Synthetic construct

<400> SEQUENCE: 15
ggcgaattca cgatgtgctg cggtgttgca cagatgcg                     38

<210> SEQ ID NO 16
<211> LENGTH: 35
<212> TYPE: DNA
<213> ORGANISM: Artificial Sequence
<220> FEATURE:
<223> OTHER INFORMATION: Synthetic construct

<400> SEQUENCE: 16
gccgaattca cgatggccgc cgaggagatg aaggc                        35

<210> SEQ ID NO 17
<211> LENGTH: 33
<212> TYPE: DNA
<213> ORGANISM: Artificial Sequence
<220> FEATURE:
<223> OTHER INFORMATION: Synthetic construct

<400> SEQUENCE: 17
cgggaattcg aggctatgct tctgtctcca cct                          33

<210> SEQ ID NO 18
<211> LENGTH: 41

```
<212> TYPE: DNA
<213> ORGANISM: Artificial Sequence
<220> FEATURE:
<223> OTHER INFORMATION: Synthetic construct

<400> SEQUENCE: 18
gcgaattcgc caccatggcg gatatcatcg caagactccg g                    41

<210> SEQ ID NO 19
<211> LENGTH: 38
<212> TYPE: DNA
<213> ORGANISM: Artificial Sequence
<220> FEATURE:
<223> OTHER INFORMATION: Synthetic construct

<400> SEQUENCE: 19
gcgaattcgc caccatgctg aaggtggaga gccctggc                        38
```